United States Patent
Goumon et al.

(10) Patent No.: US 10,449,235 B2
(45) Date of Patent: Oct. 22, 2019

(54) USE OF CREATINE KINASE AND DERIVED PEPTIDES THEREOF TO RELIEVE PAIN

(71) Applicants: CENTRE NATIONAL DE LA RECHERCHE SCIENTIFIQUE, Paris (FR); UNIVERSITÉ DE STRASBOURG, Strasbourg (FR)

(72) Inventors: Yannick Goumon, Strasbourg (FR); Jinane Mouheiche, Louvain-la-Neuve (BE); Alexis Laux-Biehlmann, Berlin (DE); Pierrick Poisbeau, Schiltigheim (FR); Nisrine Kamoun, Benfeld (FR)

(73) Assignees: CENTRE NATIONAL DE LA RECHERCHE SCIENTIFIQUE, Paris (FR); UNIVERSITÉ DE STRASBOURG, Strasbourg (FR)

( * ) Notice: Subject to any disclaimer, the term of this patent is extended or adjusted under 35 U.S.C. 154(b) by 0 days.

(21) Appl. No.: 15/556,250

(22) PCT Filed: Mar. 7, 2016

(86) PCT No.: PCT/EP2016/054816
§ 371 (c)(1),
(2) Date: Sep. 6, 2017

(87) PCT Pub. No.: WO2016/142349
PCT Pub. Date: Sep. 15, 2016

(65) Prior Publication Data
US 2018/0264088 A1    Sep. 20, 2018

(30) Foreign Application Priority Data

Mar. 6, 2015   (EP) .................................... 15305349

(51) Int. Cl.
| | |
|---|---|
| *A61K 38/45* | (2006.01) |
| *A61K 45/06* | (2006.01) |
| *A61P 29/00* | (2006.01) |
| *A61K 31/485* | (2006.01) |

(52) U.S. Cl.
CPC ............ *A61K 38/45* (2013.01); *A61K 31/485* (2013.01); *A61K 45/06* (2013.01); *A61P 29/00* (2018.01); *C12Y 207/03002* (2013.01)

(58) Field of Classification Search
CPC .. A61K 2300/00; A61K 31/485; A61K 38/45; A61K 45/06; C07D 207/408; A61P 29/00; C12Y 207/03002
See application file for complete search history.

(56) References Cited

U.S. PATENT DOCUMENTS

2007/0265221 A1    11/2007  Weiss et al.
2009/0143417 A1*    6/2009  Smith .................. A61K 31/137
                                                          514/282

FOREIGN PATENT DOCUMENTS

| FR | 2971161 A1 | | 8/2012 |
|---|---|---|---|
| WO | WO03/068949 | * | 8/2003 |

OTHER PUBLICATIONS

"Licensing Opportunities CNRS patent portfolio related to Central Nervous System Disorders," Jan. 1, 2014, XP055191985, Retrieved from the Internet: URL:http://www.fist.fr/CNRS CNS disorders patent portfolio Jan. 2014.pdf, [retrieved on May 28, 2015], Reference 04170-01.
Mouheiche, J., "Nouvelles données sur la morphine, son catabolisme et sa protéine de liaison dans le système nerveux central," Dec. 22, 2014, XP055191994, Retrieved from the Internet: URL:http://www.theses.fr/2014STRAJ022, [retrieved on May 28, 2015], pp. 1-2.
International Search Report for PCT Patent App. No. PCT/EP2016/054816 dated Apr. 22, 2016.
Written Opinion for PCT Patent App. No. PCT/EP2016/054816 dated Apr. 22, 2016.

* cited by examiner

*Primary Examiner* — Marcela M Cordero Garcia
(74) *Attorney, Agent, or Firm* — Kenealy Vaidya LLP

(57) ABSTRACT

Some embodiments are directed to the use of creatine kinase or fragments thereof which induce analgesia, and also to the use of pharmaceutical compositions including the same, to relieve pain.

11 Claims, 8 Drawing Sheets

Specification includes a Sequence Listing.

A

B

C

SEQUENCE LISTING

```
<160> NUMBER OF SEQ ID NOS: 5

<210> SEQ ID NO 1
<211> LENGTH: 381
<212> TYPE: PRT
<213> ORGANISM: Mus musculus

<400> SEQUENCE: 1

Met Pro Phe Ser Asn Ser His Asn Ala Leu Lys Leu Arg Phe Pro Ala
1               5                   10                  15

Glu Asp Glu Phe Pro Asp Leu Ser Ala His Asn Asn His Met Ala Lys
                20                  25                  30

Val Leu Thr Pro Glu Leu Tyr Ala Glu Leu Arg Ala Lys Ser Thr Pro
            35                  40                  45

Ser Gly Phe Thr Leu Asp Asp Val Ile Gln Thr Gly Val Asp Asn Pro
    50                  55                  60

Gly His Pro Tyr Ile Met Thr Val Gly Cys Val Ala Gly Asp Glu Glu
65                  70                  75                  80

Ser Tyr Glu Val Phe Lys Asp Leu Phe Asp Pro Ile Ile Glu Asp Arg
                85                  90                  95

His Gly Gly Tyr Lys Pro Ser Asp Glu His Lys Thr Asp Leu Asn Pro
                100                 105                 110
```

Asp Asn Leu Gln Gly Gly Asp Leu Asp Pro Asn Tyr Val Leu Ser
            115                 120                 125

Ser Arg Val Arg Thr Gly Arg Ser Ile Arg Gly Phe Cys Leu Pro Pro
    130                 135                 140

His Cys Ser Arg Gly Glu Arg Arg Ala Ile Glu Lys Leu Ala Val Glu
145                 150                 155                 160

Ala Leu Ser Ser Leu Asp Gly Asp Leu Ala Gly Arg Tyr Tyr Ala Leu
                165                 170                 175

Lys Ser Met Thr Glu Ala Glu Gln Gln Gln Leu Ile Asp Asp His Phe
            180                 185                 190

Leu Phe Asp Lys Pro Val Ser Pro Leu Leu Leu Ala Ser Gly Met Ala
        195                 200                 205

Arg Asp Trp Pro Asp Ala Arg Gly Ile Trp His Asn Asp Asn Lys Thr
210                 215                 220

Phe Leu Val Trp Val Asn Glu Glu Asp His Leu Arg Val Ile Ser Met
225                 230                 235                 240

Gln Lys Gly Gly Asn Met Lys Glu Val Phe Thr Arg Phe Cys Thr Gly
                245                 250                 255

Leu Thr Gln Ile Glu Thr Leu Phe Lys Ser Lys Asp Tyr Glu Phe Met
            260                 265                 270

Trp Asn Pro His Leu Gly Tyr Ile Leu Thr Cys Pro Ser Asn Leu Gly
        275                 280                 285

Thr Gly Leu Arg Ala Gly Val His Ile Lys Leu Pro Asn Leu Gly Lys
    290                 295                 300

His Glu Lys Phe Ser Glu Val Leu Lys Arg Leu Arg Leu Gln Lys Arg
305                 310                 315                 320

Gly Thr Gly Gly Val Asp Thr Ala Ala Val Gly Gly Val Phe Asp Val
                325                 330                 335

Ser Asn Ala Asp Arg Leu Gly Phe Ser Glu Val Glu Leu Val Gln Met
            340                 345                 350

Val Val Asp Gly Val Lys Leu Leu Ile Glu Met Glu Gln Arg Leu Glu
        355                 360                 365

Gln Gly Gln Ala Ile Asp Asp Leu Met Pro Ala Gln Lys
    370                 375                 380

<210> SEQ ID NO 2
<211> LENGTH: 75
<212> TYPE: PRT
<213> ORGANISM: Artificial Sequence
<220> FEATURE:
<223> OTHER INFORMATION: Peptide P1

<400> SEQUENCE: 2

Met Pro Phe Ser Asn Ser His Asn Thr Gln Lys Leu Arg Phe Pro Ala
1               5                   10                  15

Glu Asp Glu Phe Pro Asp Leu Ser Ser His Asn Asn His Met Ala Lys
            20                  25                  30

Val Leu Thr Pro Glu Leu Tyr Ala Glu Leu Arg Ala Lys Cys Thr Pro
        35                  40                  45

Ser Gly Phe Thr Leu Asp Asp Ala Ile Gln Thr Gly Val Asp Asn Pro
    50                  55                  60

Gly His Pro Tyr Ile Met Thr Val Gly Ala Val
65                  70                  75

<210> SEQ ID NO 3

```
<211> LENGTH: 75
<212> TYPE: PRT
<213> ORGANISM: Artificial Sequence
<220> FEATURE:
<223> OTHER INFORMATION: Peptide P4

<400> SEQUENCE: 3

Gln Gln Gln Leu Ile Asp Asp His Phe Leu Phe Asp Lys Pro Val Ser
1               5                   10                  15

Pro Leu Leu Leu Ala Ser Gly Met Ala Arg Asp Trp Pro Asp Ala Arg
                20                  25                  30

Gly Ile Trp His Asn Asp Asn Lys Thr Phe Leu Val Trp Ile Asn Glu
            35                  40                  45

Glu Asp His Leu Arg Val Ile Ser Met Gln Lys Gly Gly Asn Met Lys
        50                  55                  60

Glu Val Phe Thr Arg Phe Cys Thr Gly Leu Thr
65                  70                  75

<210> SEQ ID NO 4
<211> LENGTH: 25
<212> TYPE: PRT
<213> ORGANISM: Artificial Sequence
<220> FEATURE:
<223> OTHER INFORMATION: Peptide AI-25

<400> SEQUENCE: 4

Ala Arg Gly Ile Trp His Asn Asp Asn Lys Thr Phe Leu Val Trp Ile
1               5                   10                  15

Asn Glu Glu Asp His Leu Arg Val Ile
                20                  25

<210> SEQ ID NO 5
<211> LENGTH: 50
<212> TYPE: PRT
<213> ORGANISM: Artificial Sequence
<220> FEATURE:
<223> OTHER INFORMATION: Peptide KN-50

<400> SEQUENCE: 5

Lys Pro Val Ser Pro Leu Leu Leu Ala Ser Gly Met Ala Arg Asp Trp
1               5                   10                  15

Pro Asp Ala Arg Gly Ile Trp His Asn Asp Asn Lys Thr Phe Leu Val
                20                  25                  30

Trp Ile Asn Glu Glu Asp His Leu Arg Val Ile Ser Met Gln Lys Gly
            35                  40                  45

Gly Asn
    50
```

USE OF CREATINE KINASE AND DERIVED PEPTIDES THEREOF TO RELIEVE PAIN

CROSS REFERENCE TO RELATED APPLICATION(S)

This application is a national phase filing under 35 C.F.R. § 371 of and claims priority to PCT Patent Application No. PCT/EP2016/054816, filed on Mar. 7, 2016, which claims the priority benefit under 35 U.S.C. § 119 of European Patent Application No. 15305349.1, filed on Mar. 6, 2015, the contents of each of which are hereby incorporated in their entireties by reference.

BACKGROUND

Some embodiments relate to the use of creatine kinase or fragments thereof which induce analgesia, and also to the use of pharmaceutical compositions including the same. In particular, two novel peptides that include or consist of the amino acid sequence 1-75 and 184-258 derived from the amino acid sequence of creatine kinase exhibit an analgesic activity, thereby proposing them as an interesting substitute for morphine. Some embodiments are directed to treat or prevent pain.

In the following description, the references in brackets ([ ]) refer to the list of references presented at the end of the text.

Creatine kinase (CK, EC 2.7.3.2), also called phosphocreatine kinase or creatine phosphokinase (CPK), is an enzyme expressed by various tissues including the brain and muscles, where it is present in cytoplasmic and mitochondrial form. There are several isoenzymes (present in the form of noncovalent dimers): CK-MM present in muscles, CK-MB found in the myocardial cells, and CK-BB which occurs in the brain. Mitochondrial CK (mtCK) also occurs. This enzyme catalyzes the reversible conversion of creatine to phosphocreatine via the use of adenosine triphosphate (ATP, FIG. 1). This enzyme is essential for the production of ATP from stored phosphocreatine. Phosphocreatine, via ATP, thus constitutes a reservoir of energy that is rapidly usable for the muscles and other organs including the brain. CK (isoforms MM and MB; dimers) is released in the blood during tissue lesions causing cellular lysis (for example in a muscle disorder such as rhabdomyolysis, muscular effort, myocardial infarction, etc.). Assaying isoenzymes in the blood makes it possible to differentiate the origin of the cellular destruction. Thus, increase in blood CK-MB has been used in a blood test for diagnosing myocardial infarction.

In addition to its role in the metabolism of ATP, it has been recently shown that CK forms non covalent complexes of very high affinity with morphine [Patent Application FR 2 971 161] [6]. The functional consequences of this interaction are not yet clearly defined, however results show that the enzymatic activity of CK (production of ATP from phosphocreatine) is inhibited by morphine by almost 18% (FIG. 2).

Taking into account and treatment of pain are essential aspects of improving the quality of life of patients. Pain affects a considerable number of individuals, about 60 million in Europe each year, which represents an annual cost of 1 billion dollars in analgesic drugs for pain relief. The amount spent annually throughout the world on analgesic drugs was evaluated at approximately 42 billion dollars in 2010. Pain is divided up into two categories: acute pain and chronic pain. Acute pain corresponds to rapid and brief pain which is limited over time. Conversely, chronic pain is a persistent pain which can be linked, for example, to hyperalgesia, and which constitutes an enormous disease burden, affecting approximately 20% of adults and 50% of the elderly population.

The treatment of pain is based essentially on the prescription of anti-inflammatory drugs, whether they are nonsteroidal (NSAIDs) or steroidal (corticoids), and of weak or strong opiates. NSAIDs form the therapeutic class most widely prescribed throughout the world, owing to their great efficacy both on inflammation and on pain itself. They are used in all types of inflammatory pain, whether acute or chronic [Bertin and Vergne-Salle, 2007] [1]. When NSAIDs and/or corticoids are not sufficient to relieve inflammatory pain, the prescribing physician combines a non-anti-inflammatory analgesic, for example paracetamol, weak opioids (codeine, tramadol), and, if the pain continues to be resistant to the treatment, strong opioids (morphine, oxycodone, fentanyl) [Gutstein & Akil, 2006] [2].

SUMMARY

While NSAIDs are very effective, they nevertheless remain great purveyors of adverse side effects. Among the most standard adverse side effects, digestive effects are very frequent and limit the use of NSAIDs in many clinical situations. There are also renal, cutaneous, mucosal, allergic and respiratory, hematological, hepatic and, finally, neurosensory and psychological adverse side effects [Bertin and Vergne-Salle, 2007, mentioned above] [1]. In addition, NSAIDs are not effective in all types of pain. Opioids also play a major role in pain relief, but can cause hallucinatory phenomena, constipation and cardiorespiratory depression. Analgesics can also be a source of dependence (morphine, methadone, etc. . . . ). There are also cases of habituation or tolerance to analgesics, that is to say the dose necessary to obtain a constant effect must be increased. This habituation increases over time and therefore leads to the need to increase the doses and can lead to ineffectiveness of the medicament.

Indeed, the dose necessary to relieve pain can reach the toxic dose. Finally, treatment with opioids can also be associated with adverse effects including hyperalgesia when the treatment is stopped (post-operative pain, for example) [Gutstein & Akil, 2006, mentioned above; Bannister & Dickenson, 2010] [2, 3].

Furthermore despite the diversity of the existing therapeutic arsenal, many types of pain remain relatively insensitive to the known analgesics, such as neuropathic pain following damage to the nervous system (50% of patients experience no relieve), chronic visceral pain such as irritable bowel syndrome or chronic inflammatory bowel disease, fibromyalgia, pain associated with cancers and bone metastases, etc. [Yennurajalingam et al., 2004; Mizoguchi et al., 2009] [4, 5].

Research in the pharmaceutical industry on pain has over the past few years resulted only in a few limited developments. Mention may, for example, be made of triptans for migraine and certain novel medicaments of which the use still remains limited, such as the combination of tetrahydrocannabinol and cannabidiol for cancer-related and neuropathic pain. In fact, the progress made over the last two decades comes essentially from a better use and adjustments of the dosage of the available analgesics. None of the major families of these analgesics has a benefit/risk ratio which is optimal, because of a limited efficacy and/or considerable side effects.

In this context, the discovery of novel analgesics represents real progress.

The inventors were the first to unexpectedly identify peptides of creatine kinase containing binding sites for morphine only. The first two peptides identified consist of amino acids 1-75 and 184-258, sequences SEQ ID NOs: 2 and 3 respectively, of the full-length amino sequence of the mouse creatine kinase B (FIG. 3). Their functional properties were first evaluated through injections into the spinal cord of healthy mice C57B16/J in comparison to those of morphine, and showed an almost complete insensitivity of mice towards mechanical stimulation. Furthermore, using the "cuff" neuropathic rat model and the calibrated clamp test, an intrathecal injection of the peptide of amino acids 184-258 reveals that the peptide reverses the neuropathic pain (ipsilateral paw) at the mechanical level for at least 6 h. Two other peptides identified consist of amino acids 214-238 and 196-246, sequences SEQ ID NOs: 4 and 5 respectively, of the full-length amino sequence of the mouse creatine kinase B, and present analgesic activity.

These results allow considering use of these peptides derived from creatine kinase as a substitute for morphine or as adjuvant of current analgesic treatments.

Some embodiments are thus directed to a peptide including at least, or consisting of, or including a peptide consisting of, 5, 10, 15, 25, 35, 45, 55, 65 or 75 amino acids of the amino acid sequence of creatine kinase and having an analgesic activity, for use as an analgesic drug. For example, such peptides include a peptide consisting of 5 to 75, preferably 25 to 75 amino acids, of the amino acid sequence of creatine kinase, and are listed in the table below:

| SEQ ID NO: 2 | MPFSNSHNTQKLRFPAEDEFPDLSSHNNHMAK VLTPELYAELRAKCTPSGFTLDDAIQTGVDNP GHPYIM TVGAV |
|---|---|
| SEQ ID NO: 3 | QQQLIDDHFLFDKPVSPLLLASGMARDWPDAR GIWHNDNKTFLVWINEEDHLRVISMQKGGNMK EVF TRFCTGLT |
| SEQ ID NO: 4 | ARGIWHNDNKTFLVWINEEDHLRVI |
| SEQ ID NO: 5 | KPVSPLLLASGMARDWPDARGIWHNDNKTFLV WINEEDHLRVISMQKGGN |

"Creatine kinase" means, in the sense of some embodiments, the CK-MM present in the muscles, the CK-MB found in the myocardial cells, the CK-BB that occurs in the brain and the mtCK (sarcomere and ubiquitous) which is present in the mitochondria of mammalian cells, as well as the monomers of CK (CK-B and CK-M).

Preferably the drug is an analgesic, for example intended for the prevention or treatment of pain.

"Pain" means, in the sense of some embodiments, acute or chronic pain resulting for example from arthritis, neuropathy, cancer treatments induced pain, fibromyalgia or an old injury, etc. . . . .

Preferably the drug is administered parenterally, namely locoregionally or centrally (intraperitoneally, peridurally, intrathecally, intracerebroventricularly, intradermally, etc.) and systemically (intramuscularly, intravenously, subcutaneously, etc.), orally, locally (transcutaneously, etc.) or via the respiratory route (inhalation, instillation, etc.). Most preferentially, the medicament is administered intrathecally, peridurally, intracerebroventricularly, intraperitoneally or subcutaneously. In particular the drug is administered centrally, subcutaneously, transcutaneously, systemically, orally or via the respiratory route.

Preferably the peptide includes or consists of at least about 5, 10, 15, 25, 35, 45, 55, 65 or 75 amino acids of SEQ ID NO: 1, more preferably includes 5 to 75, 25 to 75 amino acids of SEQ ID NO: 1.

Preferably the peptide includes or consists of the sequence SEQ ID NO: 2, SEQ ID NO: 3, SEQ ID NO: 4 and/or SEQ ID NO: 5. Another subject of some embodiments is also a peptide including at least, or consisting of, or including a peptide consisting of, 5, 10, 15, 25, 35, 45, 55, 65 or 75 amino acids of the amino acid sequence of creatine kinase and having an analgesic activity, for a use in the prevention or treatment of pain.

Preferably the peptide includes or consists of an amino acid sequence of at least about 5, 10, 15, 25, 35, 45, 55, 65 or 75 amino acids of SEQ ID NO: 1, more preferably includes 5 to 75, 25 to 75 amino acids of SEQ ID NO: 1.

Preferably the peptide includes or consists of the sequence SEQ ID NO: 2, SEQ ID NO: 3, SEQ ID NO: 4 and/or SEQ ID NO: 5.

Some other embodiments are directed to a pharmaceutical composition for a use in the prevention or treatment of pain, the composition including a least a peptide as defined in some embodiments and a pharmaceutically acceptable vehicle. The composition may further include one or more other analgesic compound(s).

"Analgesic compound" means, in the sense of some embodiments, general opiate compounds, i.e., compounds that act on opioid receptors. They are generally used to treat severe and long-lasting pain. Preferably, these are morphine compounds, notably morphine or morphinomimetic compounds, i.e., compounds that are derived from morphine and/or that act on morphine receptors and/or that recruit one or more metabolic pathways common to morphine. As particular examples, mention may be made of the following compounds in particular: morphine, fentanyl, sufentanil, alfentanyl, heroin, oxycodone, hydromorphone, levorphanol, methadone, buprenorphine, butorphanol, meperidine, etc . . . .

Preferably the pharmaceutical includes the peptide including or consisting of the sequence SEQ ID NO 2, SEQ ID NO: 3, SEQ ID NO: 4 and/or 5, eventually in combination with morphine.

Some other embodiments are directed to a peptide including, or consisting of, or including a peptide consisting of, 5 to 75 amino acids, preferably 25 to 75 amino acids, of the full-length amino acid sequence of creatine kinase, and having an analgesic activity. Preferably the peptide of 25 to 75 amino acids includes the sequence SEQ ID NO: 2, SEQ ID NO: 3, SEQ ID NO: 4 and/or SEQ ID NO: 5.

Some other embodiments are directed to a variant of a peptide of some embodiments (by deletion, addition and/or substitution of amino acid(s)), the variant having at least 85%, preferably at least 90%, more preferably at least 95%, sequence identity with the full-length sequence SEQ ID NO: 2 or SEQ ID NO: 3, preferably SEQ ID NO: 2, and retaining an analgesic activity, Some other embodiments are directed to a nucleic acid encoding the sequence SEQ ID NO: 2, SEQ ID NO: 3, SEQ ID NO: 4 and/or SEQ ID NO: 5 or a variant thereof as defined above; the nucleic acid corresponding to RNA or DNA, preferably to DNA.

Some other embodiments are directed to a vector or host cell including a nucleic acid of some embodiments. Such (expression) vectors and host cells are well known in the art.

Other advantages may also occur to a of ordinary skill in the art upon reading the example below, illustrated by the attached figures, given for illustrative purposes.

EXAMPLES

Example 1

Identification of Peptides from Creatine Kinase Containing Binding Sites for Morphine Only In order to characterize the fragment of CK that can bind morphine/morphine metabolites, six overlapping mouse CK-B-derived peptides (73 to 96 residues) have been synthesized (Proteogenix, Schiltigheim, France): CK-B1-75, CK-B65-140, CK-B127-199, CK-B184-258, CK-B248-343, CK-B286-381.

Determination of the affinity and specificity for alkaloids was done on a 96-well plate (NUNC, Roskilde, Denmark) coated 90 min at 37° C. with 100 µl of a 10 µg/ml of the corresponding peptide solution in carbonate-bicarbonate buffer (CA buffer, 15 mM $Na_2CO_3$, 35 mM $NaHCO_3$, pH9.6). After three washes with 0.1 M NaCl/Pi-0.05% Tween 20 buffer (PT; 10 min), wells were incubated for 30 min with 200 µl of bovine serum albumin (BSA) diluted in NaCl/Pi buffer (5%, w/v) in order to saturate nonspecific sites. After saturation, wells were incubated for 1 h at 37° C. with 100 µl of NaCl/Pi-BSA (3%, w/v) containing from 300 µM to 0.1 µM of the following potential CK-ligands: morphine (Sigma-Aldrich), M6G (Sigma-Aldrich), M3G (Sigma-Aldrich), codeine (Sigma-Aldrich). Then, the plate was washed three times with PT buffer, and 100 µl of the primary antibody (6D6, 1: 2,000, v/v; Aviva Systems Biology, ref. AMM00043) were added in each well. After three more washes with PT buffer, 100 µl of the secondary antibody (HRP-conjugated donkey anti-mouse IgG, P.A.R.I.S.; dilution 1:2,000) were added and left in the wells for 30 min at room temperature (RT). After two washes with PT buffer followed by two washes with a pH 7.5 phosphate-citrate-0.05% Tween 20 buffer (CT buffer, 10 min), revelation was performed with 200 µl of a fresh solution of ortho-phenylene diamine (Sigma Aldrich) at 1.5 mg/ml in CT buffer containing 0.075% hydrogen peroxide. After 20 min of incubation at RT, optical density was determined at 410 nm with a Multiskan EX plate reader (Thermo Life Sciences, Cergy Pontoise, France).

Two peptides containing binding sites for morphine only were identified: peptide P1 consisting of amino acids 1-75 (SEQ ID NO: 2) from the mouse CK-B sequence SEQ ID NO: 1, and peptide P4 consisting of amino acids 184-258 (SEQ ID NO: 3) of the mouse CK-B sequence SEQ ID NO: 1.

Figure 1:
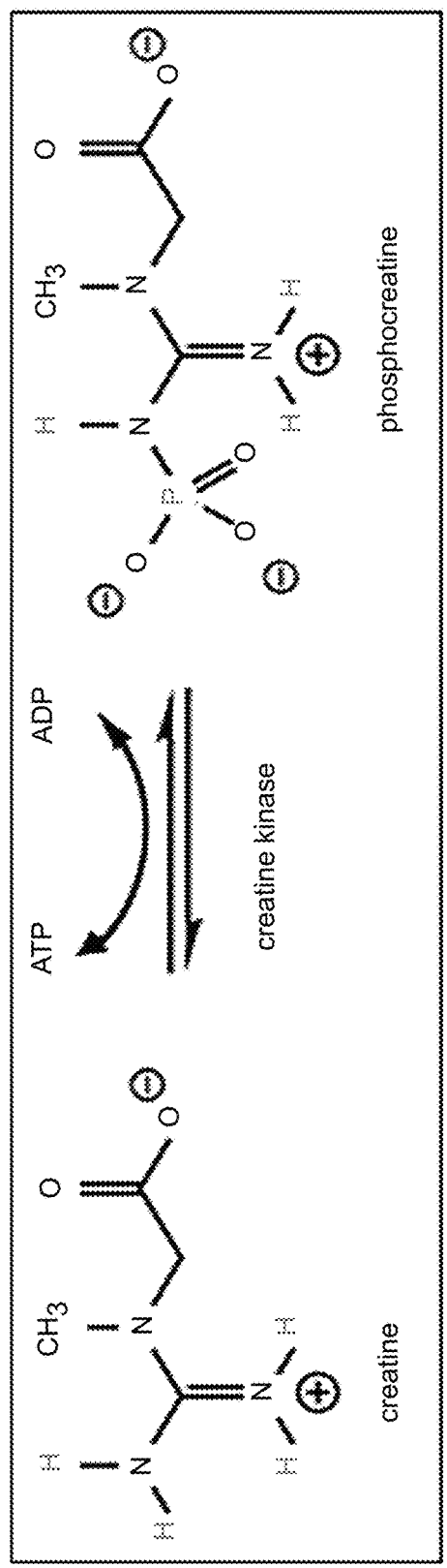
FIG. 1 represents the enzymatic reaction catalyzed by creatine kinase.
Figure 2:
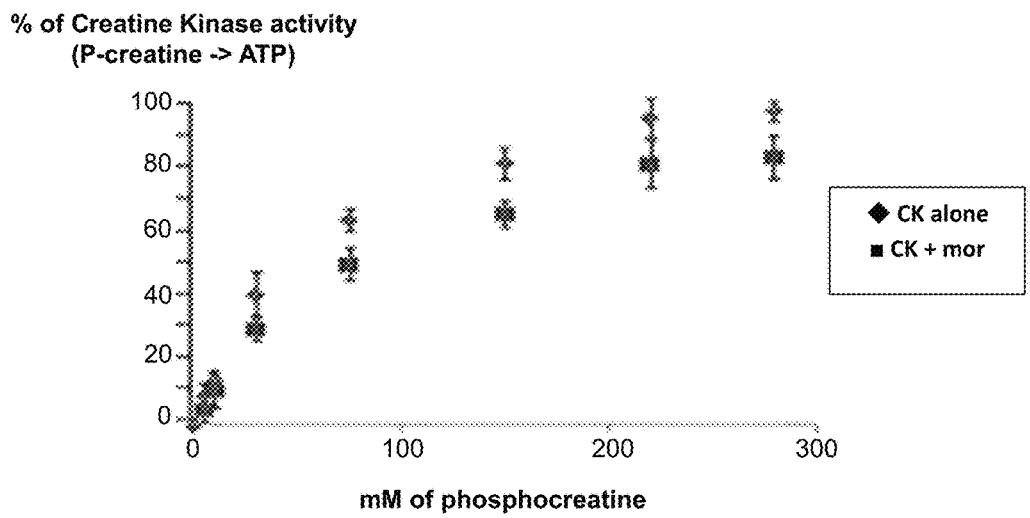
FIG. 2 represents the inhibitory effect of morphine of the ATP formation by CK-M (ratio 3n/1n).
Figure 3:
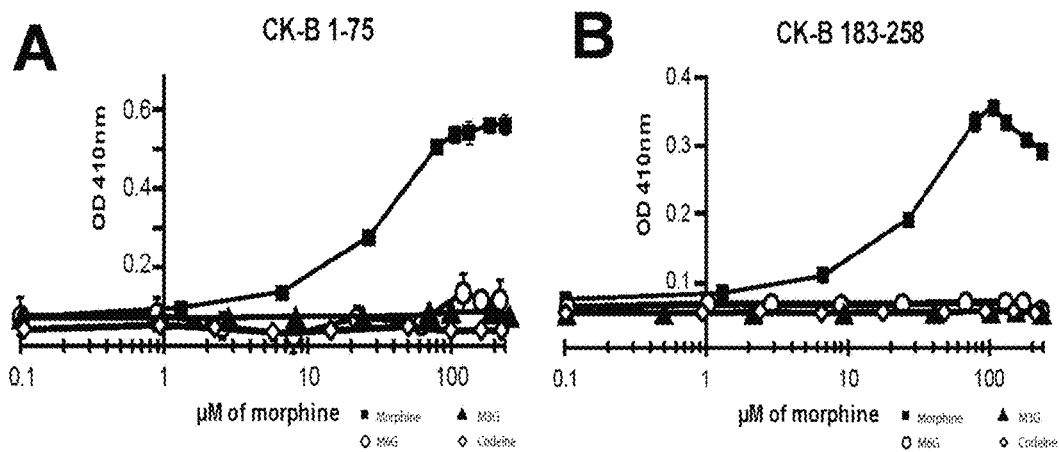
FIG. 3 represents ELISA tests showing affinity for morphine of (A) peptide P1 (amino acids 1-75 of mouse CK-B) for morphine, and (B) peptide P4 (amino acids 184-258 of mouse CK-B).

The results are shown in FIG. 3.

Peptides P1 and P4 showed an affinity for morphine but not for metabolites thereof (M3G and M6G) and codeine, thereby indicating that peptides P1 and P4 only contain binding sites for morphine.

Example 2

Effect of Intrathecal Injections of Morphine, Peptides P1 and P4 on Mechanical Nociceptive Thresholds of Healthy Mice Experiments were performed on adult male C57Bl/6J mice (6 weeks old, Charles River, L'Arbresle, France). Animals were housed in groups of 3, under standard conditions (room temperature: 22° C.; 12/12-hour light-dark cycle) with ad libitum access to food and water. All experiments were conducted according to the recommendations of the European Committee Council Direction of Sep. 22, 2010 (2010/63/EU).

The functional properties of peptides P1 (20 nmoles) and P4 (10 nmoles) were evaluated through injections in the spinal cord of 4 groups of 6 mice C57B16/J (intrathecal injection, volume of 5 µl). The aim was to study the consequences of these injections on nociceptive thresholds in comparison of low concentrations of morphine (MOR, 10 nmoles) and saline solution (SAL, control), using the von Frey filaments test. Mice were previously placed under gaseous anesthesia with isoflurane (volatile anesthetic agent) with a minimum alveolar concentration (MAC) of 1.34%. A 27-gauge needle connected to a syringe was inserted between the vertebrae L5 and L6, in the subarachnoid space. Isoflurane induced a general anesthesia with respiratory depression in mice.

The mechanical threshold for hind paw withdrawal was determined using Von Frey hairs. Mice were placed in clear plexiglass boxes on an elevated mesh screen. Von Frey filaments (Bioseb, Chaville, France) were applied to the plantar surface of each hind paw in a series of ascending forces (0.4 g-15 g). Filaments were tested 5 times per paw, and the mechanical threshold was defined as 3 or more withdrawals out of the 5 trials. Lithium chloride and naloxone (Sigma-Aldrich, St. Louis, U.S.A.) were diluted in NaCl 0.9% (w/v).

When using the von Frey filaments test, naive mice showed basic mechanical nociceptive thresholds around 6 g for both hind legs (=pre-test).

Figure 4:
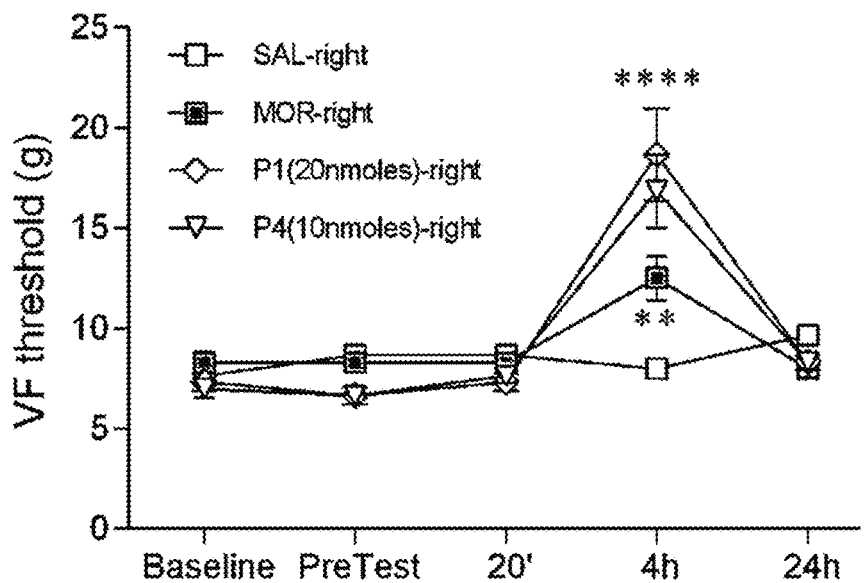
FIG. 4 represent effect of saline solution (SAL-right), morphine (MOR-right), peptides P1 (P1(20 nmoles)-right) and P4 (P4(10 nmoles)-right) on mechanical nociceptive thresholds of mice using von Frey filaments. n=6 for each group, statistical analysis: two-ways ANOVA, Holm-Sidak p<0.01, **p<0.0001.

The results regarding right hind paw are shown in FIG. 4.

Compared to the pre-test before injection, injection of saline solution 0.9% did not affect the nociceptive thresholds (control). Unlike the observed threshold for the control, injections of morphine (10 nmoles), peptides P1 (20 nmoles) and P4 (10 nmoles) induced a significant analgesia (two-ways ANOVA for repeated measures, interaction time against treatment for right leg, $F(44,220)=6.243$, $p<0.0001$). At a low dose of 10 nmoles and 4 hours after injection, morphine induced a significant analgesia on right leg (multiple comparison test of Holm-Sidak, $p<0.01$). Analgesia was even stronger for peptides P1 and P4 (Holm-Sidak, $p<0.0001$). For both peptides, the values of von Frey were close or equal to cut-off, namely a value allowing to conclude to an almost complete insensitivity of mice towards mechanical stimulation.

Figure 5:
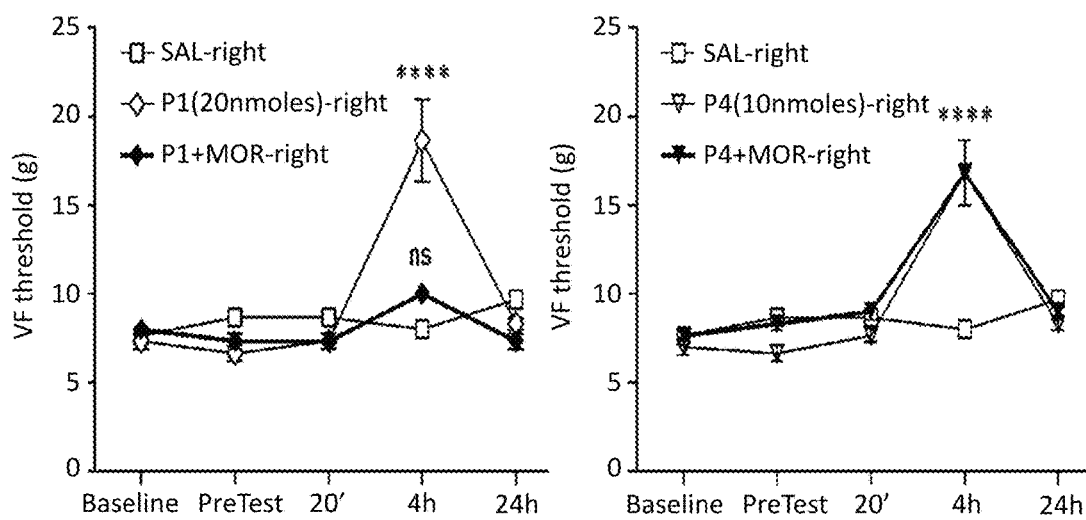
FIG. 5 represents effect of morphine (10 nmoles) on analgesic activity of (A) peptide P1 (20 nmoles) and (B) peptide P4 (10 nmoles).

Furthermore, when injections were carried out in presence of morphine (FIG. 5), it was significant to note occlusion of analgesic activity of peptide P1 (20 nmoles) by 10 nmoles of morphine while this property was not observed for peptide P4 injected at 10 nmoles.

Example 3

Effect of Intrathecal Injections of Peptides P1 and P4 on Mechanical Nociceptive Thresholds of Neuropathic Rats Model Experiments were performed on adult male Wistar at (6 weeks old, Charles River, L'Arbresle, France). Animals were housed in groups of 3, under standard conditions (room temperature: 22° C.; 12/12-hour light-dark cycle) with ad libitum access to food and water. All experiments were conducted according to the recommendations of the European Committee Council Direction of Sep. 22, 2010 (2010/63/EU). Procedures were positively evaluated by the regional ethical committee, and experiments were conducted with an official authorization for animal experimentation from the French Department of Agriculture (license 67-116 to P.P.).

All surgeries were done under aseptic conditions and ketamine/xylazine anaesthesia (ketamine: 17 mg/ml, xylazine: 2.5 mg/ml, i.p., 4 ml/kg, i.p.; Centravet, Taden, France). The right sciatic nerve was cuffed with a section of polyethylene tubing (cuff group) as previously described [Mosconi et Kruger, Pain, 64(1): 37-57, 1996] [7]. Sham-operated mice underwent the same surgical procedure as cuffed animals without implantation of the cuff (sham group).

The functional property of peptide P4 (10 nmoles) was evaluated through injections in the spinal cord of 1 groups of 3 rats (intrathecal injection, volume of 5 μl). The aim was to study the consequences of these injections on mechanic nociceptive threshold of cuffed animals in comparison of the sham group (control), using the calibrated forceps test. Rats were previously placed under gaseous anesthesia with iso-flurane (volatile anesthetic agent) with a minimum alveolar concentration (MAC) of 1.34%. A 27-gauge needle connected to a syringe was inserted between the vertebrae L5 and L6, in the subarachnoid space.

The mechanical response was evaluated using digital calibrated forceps (Bioseb, Chaville, France) according to company's recommendations, before and 1 to 6 hours after intrathecal injections.

Figure 6:
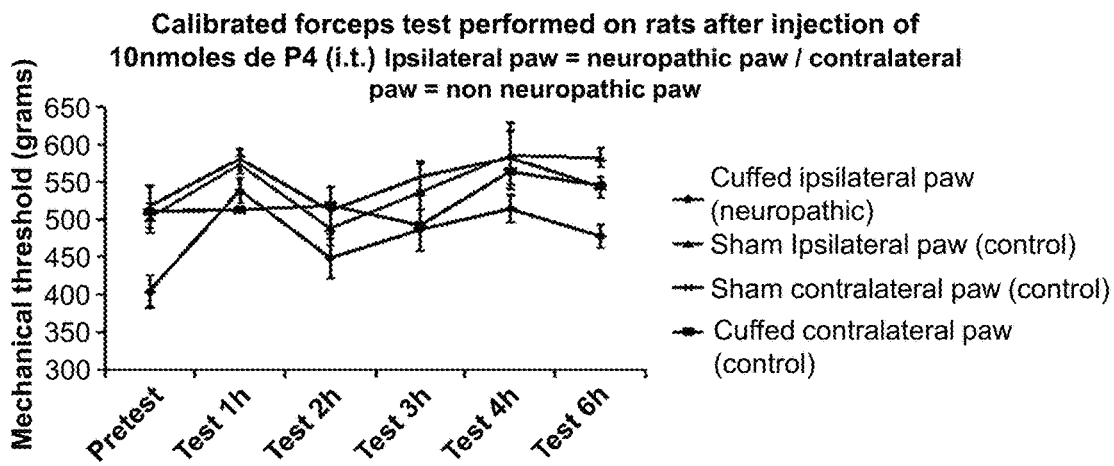
FIG. 6 represents effect of intrathecal (IT) injection of peptide P4 (10 nmoles) on mechanical threshold of rats using the calibrated forceps test (A), and mechanical thresholds of the ipsilateral (=neuropathic paw) (B) or of the contralateral (=non neuropathic paw) (C) of cuffed rats before and after injection of the peptide P4.
Figure 6:
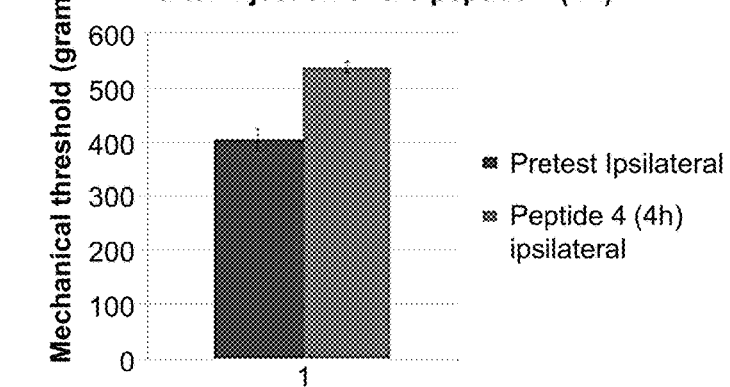
Figure 6:
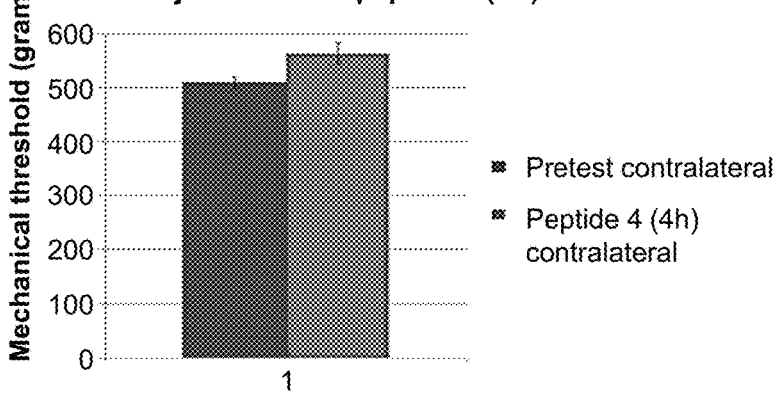

The results at $T_{+4h}$ are shown in FIG. 6.

The intrathecal injection of 10 nmoles of the peptide 4 revealed that the peptide reversed the neuropathic pain (ipsilateral paw) at the mechanical level. However peptide 4 did not affect both the non-cuffed contralateral paw mechanical threshold and the sham group. This analgesia lasted for at least 6 h.

Example 4

Effect of Intraperitoneal Injections of Morphine, Peptides P1 and P4 on Mechanical Nociceptive Thresholds of Neuropathic Mice Experiments were performed on adult male C57Bl/6J mice (6 weeks old, Charles River, L'Arbresle, France). Animals were housed in groups of 5, under standard conditions (room temperature: 22° C.; 12/12-hour light-dark cycle) with ad libitum access to food and water. All experiments were conducted according to the recommendations of the European Committee Council Direction of Sep. 22, 2010 (2010/63/EU).

All surgeries were done under aseptic conditions and ketamine/xylazine anaesthesia (ketamine: 17 mg/ml, xylazine: 2.5 mg/ml, i.p., 4 ml/kg, i.p.; Centravet, Taden, France). The right sciatic nerve was cuffed with a section of polyethylene tubing (cuff group) as previously described [Mosconi et Kruger, Pain, 64(1): 37-57, 1996] [7].

The functional properties of peptide P4 (10 nmoles), NaCl 0.9% and morphine (10 nmoles) were evaluated through intraperitoneal injection to C57Bl6/J neuropathic mice (10 nmole in a volume of 300 μl). The aim was to study the consequences of P4 injections on nociceptive thresholds in comparison of low concentrations of morphine (MOR, 10 nmoles) and NaCl solution (control). The mechanical threshold for hind paw withdrawal was determined using Von Frey hairs. Mice were placed in clear plexiglass boxes on an elevated mesh screen. Von Frey filaments (Bioseb, Chaville, France) were applied to the plantar surface of each hind paw in a series of ascending forces (0.4 g-15 g). Filaments were tested 5 times per paw, and the mechanical threshold was defined as 3 or more withdrawals out of the 5 trials.

Figure 7:
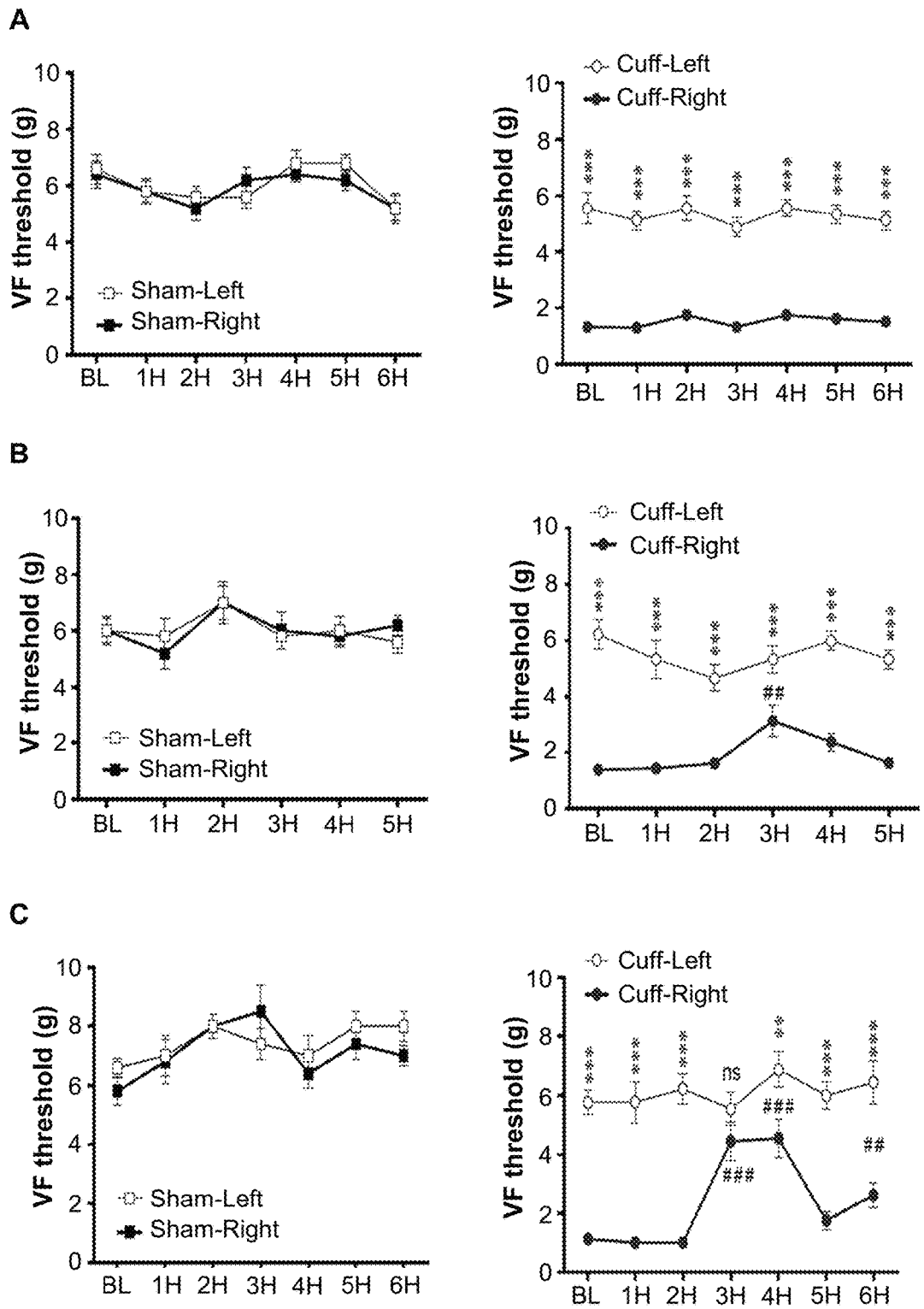
FIG. 7 represents effect of intraperitoneal injection of peptide P4 (C) vs saline solution (A) and morphine (B) on mechanical thresholds of neuropathic mice using von Frey filaments. Comparison to baseline (BL), Tukey multiple comparison posthoc, # #=p<0.01, ###=p<0.001, n=10 for each groups.

The results are shown in FIG. 7.

When using the von Frey filaments test, NaCl injected mice showed basic mechanical nociceptive thresholds around 6 g for contralateral hind legs (BL=pre-test), whereas the ipsilateral paw always show a nociceptive thresholds around 1-2 g (FIG. 7A). No effect was observed for Sham animals.

Morphine (10 nmoles) injections to mice do not modify basic mechanical nociceptive thresholds of the contralateral hind legs (BL=pre-test), whereas a significant analgesic effect is observed at 3 h for the ipsilateral paw (comparison to baseline (BL), Tukey multiple comparison posthoc, # #=$p<0.01$) (FIG. 7B). No significant effect was observed for the Sham group.

P4 (10 nmoles) injections to mice do not modify basic mechanical nociceptive thresholds of the contralateral hind legs (BL=pre-test), whereas a significant analgesic effect is observed at 3 h and 4 h post injection for the ipsilateral paw (comparison to baseline (BL), Tukey multiple comparison posthoc, # #=p<0.01, ###=p<0.001) (FIG. 7C). No significant effect was observed for Sham animals.

Example 5

Effect of Intrathecal Injections of a Peptide AI-25 on Mechanical Nociceptive Thresholds of Neuropathic Mice A peptide derived from the peptide P4 has been synthesized (Proteogenix, Schiltigheim, France): AI-25 corresponding to amino acids 214-238 (SEQ ID NO: 4) of the full-length amino sequence of the mouse creatine kinase B.

Experiments and surgeries were performed as previously described.

The functional property of peptide AI-25 (10 nmoles) was evaluated through injections in the spinal cord of 8 mice C57B16/J (intrathecal injection, volume 5 µl). The aim was to study the consequences of these injections on mechanical nociceptive threshold of cuffed mice using the calibrated forceps test.

The mechanical threshold for hind paw withdrawal was determined using Von Frey filaments as previously described.

Figure 8:
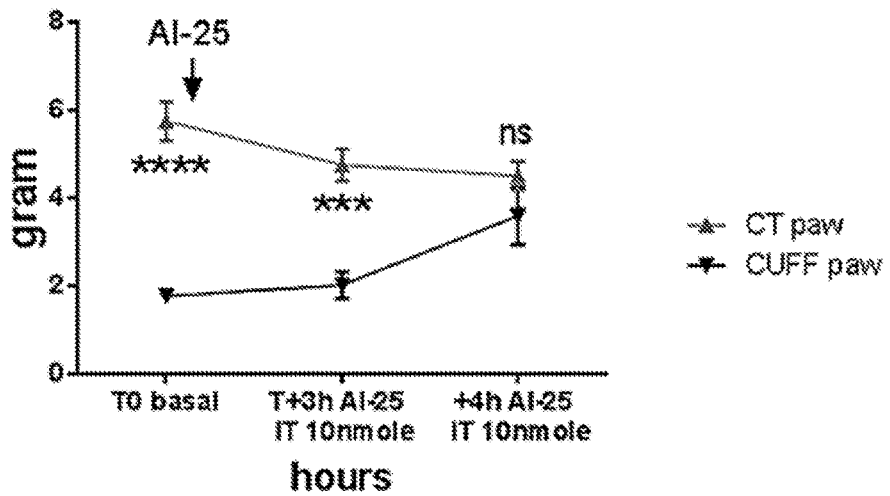
FIG. 8 represents effect of intrathecal (IT) injection of peptide AI-25 (10 nmoles) on mechanical nociceptive threshold of mice using calibrated forceps test (A), and mechanical thresholds of the ipsilateral paw (8), or of the contralateral paw (C) of cuffed mice before and after injection of the peptide AI-25.
Figure 8:
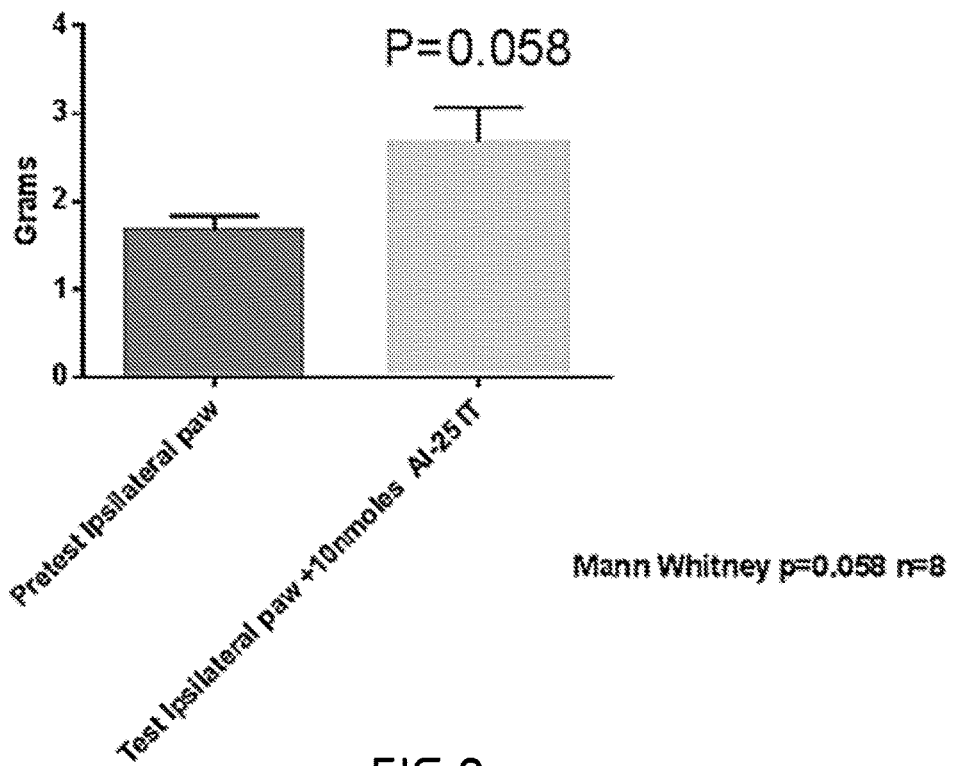
Figure 8:
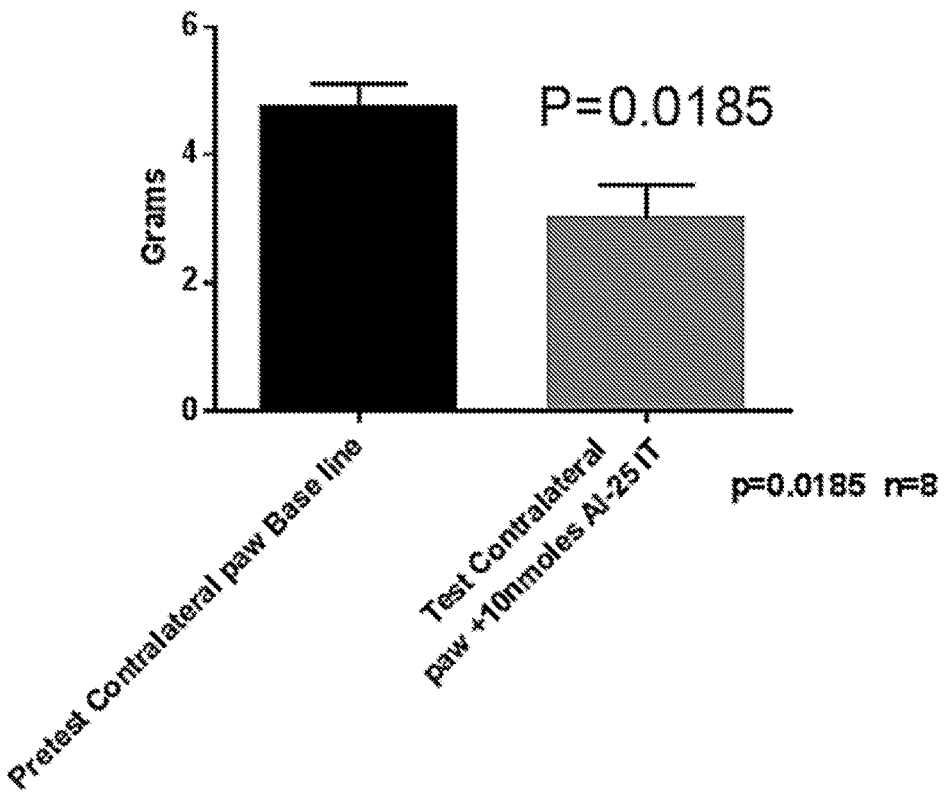

The results are shown in FIG. 8.

The intrathecal injection of 10 nmoles of the peptide AI-25 revealed that the peptide reversed the neuropathic pain (ipsilateral paw) at the mechanical level. However the peptide AI-25 did not significantly affect the non-cuffed contralateral paw mechanical threshold.

Example 6

Effect of Intrathecal Injections of a Peptide KN-50 on Mechanical Nociceptive Thresholds of Neuropathic Mice A peptide derived from the peptide P4 has been synthesized (Proteogenix, Schiltigheim, France): KN-50 corresponding to amino acids 196-246 (SEQ ID NO: 5) of the full-length amino sequence of the mouse creatine kinase B.

Experiments and surgeries were performed as previously described.

The functional property of peptide KN-50 (33 nmoles) and NaCl 0.9% was evaluated through injections in the spinal cord of 8 mice C57B16/J (intrathecal injection, volume 5 µl). The aim was to study the consequences of these injections on mechanical nociceptive threshold of cuffed mice, in comparison of saline solution.

The mechanical threshold for hind paw withdrawal was determined using Von Frey filaments as previously described.

Figure 9:
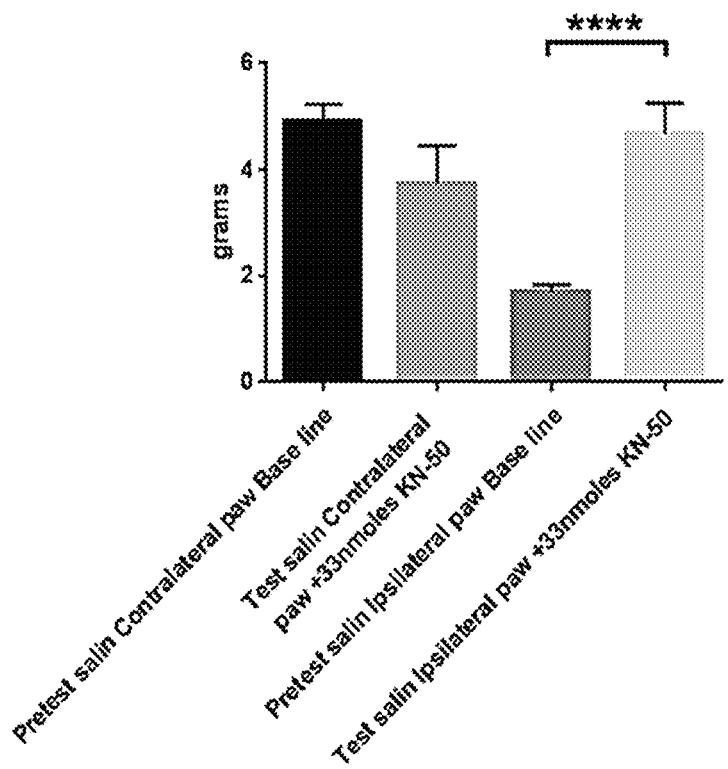
FIG. 9 represents the effect of intrathecal (IT) injection of peptide KN-50 (33 nmoles) on mechanical nociceptive threshold of the ipsilateral or contralateral paw of cuffed mice, before and after injection of the peptide KN-50, in comparison of saline solution (control).

The results are shown in FIG. 9.

The intrathecal injection of 33 nmoles of the peptide KN-50 revealed that the peptide reversed the neuropathic pain (ipsilateral paw) at the mechanical level. However the KN-50 did not affect the non cuffed contralateral paw mechanical threshold.

LIST OF REFERENCES

1. Bertin and Vergne-Salle, "Traitements médicamenteux de l'inflammation et des douleurs inflammatoires" ["Drug treatments for inflammation and inflammatory pain"] UPSA Pain Institute—A Editorial Paris, p. 113-132, 2007
2. Gutstein and Akil, "Opioid analgesics", in "The Pharmacological Basis of Therapeutics" Brunton et al., Eds. McGraw-Hill, 2006.
3. Bannister et Dickenson, Curr. Opin. Support Palliat. Care, 4: 1-5, 2010
4. Yennurajalingam et al., Support Cancer Ther., 1:97-110, 2004
5. Mizoguchi et al., Int. Rev. Neurobiol., 85: 249-260, 2009*
6. Demande de Brevet FR 2 971 161
7. Mosconi et Kruger, Pain, 64(1): 37-57, 1996

---

The invention claimed is:

1. A method of providing analgesic treatment comprising: administrating to a patient in need thereof a drug including a peptide consisting of an amino acid sequence selected from the group consisting of:
   a sequence at least 85% identical to the sequence SEQ ID NO: 2 and retaining an analgesic activity;
   a sequence at least 85% identical to the sequence SEQ ID NO: 3 and retaining an analgesic activity;
   the sequence SEQ ID NO: 4; and
   the sequence SEQ ID NO: 5.

2. The method of claim 1, further including administering the drug centrally, subcutaneously, transcutaneously, systemically, orally or via the respiratory route.

3. A method of preventing or treating pain, comprising: administrating to a patient in need thereof a drug including a peptide consisting of an amino acid sequence selected from the group consisting of:
   a sequence at least 85% identical to the sequence SEQ ID NO: 2 and retaining an analgesic activity;
   a sequence at least 85% identical to the sequence SEQ ID NO: 3 and retaining an analgesic activity;
   the sequence SEQ ID NO: 4; and
   the sequence SEQ ID NO: 5.

4. The method of claim 1, wherein said peptide consists of the sequence SEQ ID NO: 2, SEQ ID NO: 3, SEQ ID NO: 4 or SEQ ID NO: 5.

5. The method of claim 3, wherein said drug further comprises a pharmaceutically acceptable vehicle.

6. The method of claim 5, wherein the peptide consists of the sequence SEQ ID NO: 3.

7. The method of claim 3, wherein said drug further comprises at least one additional analgesic compound.

8. The method of claim 3, wherein the one or more additional analgesic compounds includes morphine.

9. A method of providing analgesic treatment comprising:
administrating to a patient in need thereof a drug comprising a peptide consisting of an amino acid sequence selected from the group consisting of:
a sequence at least 85% identical to the sequence SEQ ID NO: 2 and retaining an analgesic activity;
a sequence at least 85% identical to the sequence SEQ ID NO: 3 and retaining an analgesic activity;
the sequence SEQ ID NO: 4; and
the sequence SEQ ID NO: 5.

10. The method of claim 9, wherein said peptide consists of the sequence SEQ ID NO: 2, SEQ ID NO: 3, SEQ ID NO: 4 or SEQ ID NO: 5.

11. The method of claim 6, wherein said drug further comprises at least one additional analgesic compound.

* * * * *